(12) United States Patent
Rothacher et al.

(10) Patent No.: US 9,434,980 B2
(45) Date of Patent: Sep. 6, 2016

(54) METHOD FOR CONCENTRATING SAMPLE CONSTITUENTS AND FOR MULTIPLYING NUCLEIC ACIDS FROM A BIOLOGICAL SAMPLE WHICH ARE CONTAINED IN THE SAMPLE CONSTITUENTS

(75) Inventors: Peter Rothacher, Bruchsal (DE); Jan Weile, Leinfelden-Echterdingen (DE); Susanne Muench, Stuttgart (DE); Martina Daub, Weissach (DE)

(73) Assignee: ROBERT BOSCH GMBH, Stuttgart (DE)

( * ) Notice: Subject to any disclaimer, the term of this patent is extended or adjusted under 35 U.S.C. 154(b) by 1106 days.

(21) Appl. No.: 13/283,279

(22) Filed: Oct. 27, 2011

(65) Prior Publication Data
US 2012/0135471 A1 May 31, 2012

(30) Foreign Application Priority Data
Oct. 27, 2010 (DE) .................. 10 2010 043 015

(51) Int. Cl.
*C12P 19/34* (2006.01)
*C12Q 1/68* (2006.01)

(52) U.S. Cl.
CPC .......... *C12Q 1/6806* (2013.01); *B01L 2200/10* (2013.01)

(58) Field of Classification Search
USPC ............................................... 435/6.12, 91.2
See application file for complete search history.

(56) References Cited

U.S. PATENT DOCUMENTS

| 5,348,855 A * | 9/1994 | Dattagupta et al. ......... 435/6.14 |
| 2004/0253624 A1 | 12/2004 | Smith et al. |
| 2009/0120865 A1 | 5/2009 | Chung et al. |
| 2009/0152187 A1 | 6/2009 | Shin et al. |
| 2009/0226910 A1* | 9/2009 | Isac et al. ......................... 435/6 |
| 2010/0021925 A1* | 1/2010 | Gauch et al. ..................... 435/6 |
| 2010/0092979 A1 | 4/2010 | Kelso et al. |
| 2011/0059433 A1* | 3/2011 | Marc et al. ...................... 435/6 |

FOREIGN PATENT DOCUMENTS

| EP | 1 416 047 A1 | 5/2004 |
| EP | 0 389 063 B2 | 10/2006 |
| GB | 2 337 261 A | 11/1999 |
| WO | 99/60005 A1 | 11/1999 |
| WO | 03/062134 A1 | 7/2003 |
| WO | 2004/065010 | 8/2004 |
| WO | 2004/065010 A2 | 8/2004 |
| WO | 2006/071770 A2 | 7/2006 |
| WO | 2010/039802 A2 | 4/2010 |
| WO | 2010/040831 A1 | 4/2010 |

* cited by examiner

*Primary Examiner* — Kenneth Horlick
(74) *Attorney, Agent, or Firm* — Norton Rose Fulbright US LLP

(57) ABSTRACT

A method is disclosed for concentrating sample constituents and for multiplying nucleic acids from a biological sample which are containing in the sample constituents. The nucleic acids are amplified on the same filter on which the sample constituents are also separated off.

13 Claims, 6 Drawing Sheets

METHOD FOR CONCENTRATING SAMPLE CONSTITUENTS AND FOR MULTIPLYING NUCLEIC ACIDS FROM A BIOLOGICAL SAMPLE WHICH ARE CONTAINED IN THE SAMPLE CONSTITUENTS

This application claims priority under 35 U.S.C. §119 to German patent application no. 10 2010 043 015.3, filed on Oct. 27, 2010 in Germany, the disclosure of which is incorporated herein by reference in its entirety.

BACKGROUND

The present disclosure relates to a method for concentrating sample constituents and for multiplying the nucleic acids present in the sample constituents.

The detection of resistances to antibiotics is gaining increasing importance in infectious disease diagnostics owing to the increasing spread of said resistances, for example MRSA and fluoroquinolone resistance in *E. coli* and in bacteria which cause tuberculosis, sepsis or pneumonia.

In conventional diagnostics, said resistances are usually established using a culture-based method. However, cell culture-based resistance determination is a time-consuming method, since 2-3 days are required for culture and analysis. By analyzing bacterial DNA, resistances can be determined considerably faster. For this purpose, the DNA of the pathogens must be amplified. Amplifications of this kind can, for example, be achieved by the cooperation of DNA and RNA polymerases (nucleic acid sequence based amplification; NASBA), by polymerization and strand displacement (rolling circle amplification; RCA), or by using ligases (ligase chain reaction; LCR). However, owing to its high specificity and sensitivity, the polymerase chain reaction (PCR) is the most commonly used amplification method. In general, the nucleic acid-containing material is, for this purpose, processed and purified prior to PCR.

The processing protocols for nucleic acids envisage multiple work steps in which cells or viruses are accumulated, for example by centrifugation, and the nucleic acids are isolated by cell lysis and various wash steps.

European patent EP 0389063 B2 describes an established purification method of multiple steps, wherein DNA is bound to a solid silica-containing phase in the presence of chaotropic salts. In said method, the cells are first lysed with a chaotropic buffer. The lysate is contacted with a solid silica-containing phase, to which the DNA binds. Subsequently, the solid phase with the bound DNA is separated from the rest of the lysate and the DNA complex is washed. Lastly, depending on the end application, the DNA is eluted from the solid phase or amplified directly in the bound state.

In contrast, "micro total analysis systems" (µ total analysis system, µ TAS) offer the advantage that individual work steps are combined and automated and, at the same time, reduced to a microscale. The potential of systems of this kind lies primarily in their low power requirements, the fast reaction times and in the reduction of sample and reagent volumes, making possible an analytical laboratory on the scale of a chip ("lab-on-a-chip").

Such a microfluidic system which allows the isolation and amplification of DNA from aqueous solutions is known from WO200465010. When using said system, the sample is first filtered through a membrane, with the cells remaining on the membrane and, in the next step, being removed with the membrane from the filter chamber. After insertion of the membrane into the actual microfluidic system, the cells are washed, lysed, and subsequently the DNA is amplified, with the membrane being removed from the instrument for the amplification and, afterwards, being reinserted. Finally, the amplified DNA is detected while it flows through a channel.

However, providing a robust µ-TAS for diagnostics is made difficult not only by the many work steps between sample processing and PCR reaction, but also by the fact that it is necessary, for example for the analysis of cell- or virus-containing fluids, to have available for analysis amounts which are substantially larger than only a few drops, since media of this kind often contain only very low cell or virus numbers. For example, in the case of sepsis, only 5 pathogens may be present per ml of blood. Thus, it is necessary in the majority of cases to process relatively large sample volumes (two or more milliliters) so that there is a chance of finding enough cells or viruses in the analyte.

The resulting need to switch from macroscopic sample volumes to the desired microliter amounts in a microfluidic system is a problem.

SUMMARY

An object of the present disclosure is to provide a method for concentrating sample constituents and for multiplying nucleic acids from a biological sample which are containing in the sample constituents, which method takes place in a few individual steps and offers the possibility of automation.

It is also an object of the present disclosure to provide an apparatus for carrying out a corresponding method, which apparatus meets the requirements of automation on a microscale.

The present disclosure therefore relates to a method for concentrating sample constituents and for multiplying nucleic acids from a biological sample which are present in the sample constituents, comprising the following steps:
1) providing a biological sample in liquid form;
2) introducing the sample into a separating system having at least one filter;
3) accumulating the sample constituents containing in the sample by separating off the sample constituents on the filter;
4) adding amplification reagents; and
5) directly amplifying at least one nucleic acid present in the sample constituents.

The term "sample constituent" is to be understood hereinafter to mean both cells and viruses.

The term "cell" is to be understood hereinafter to mean both prokaryotic and eukaryotic cells.

The term "virus" is to be understood hereinafter to mean noncellular particles which contain the information regarding their propagation and spreading, but do not have any endogenous metabolism and are therefore dependent on the metabolism of a host cell. Outside the host cell, viruses exist predominantly as virions.

The term "nucleic acid present in the sample constituents" is to be understood hereinafter to mean firstly inherent (endogenous) nucleic acids, including mitochondrial nucleic acids and virion nucleic acids. However, it is also to be understood to mean secondly foreign (exogenous) nucleic acids, for example of viruses which have attacked a cell. The nucleic acids can be DNA (deoxyribonucleic acid), RNA (ribonucleic acid) or else cDNA.

A "biological sample" is considered to be any material which directly or indirectly originates from living or dead organisms and is already present in liquid form or has been dissolved such that it can be applied to the filter system.

The term "separating system" is to be understood hereinafter to mean an apparatus in which the method according to the disclosure is carried out and which comprises at least one filter. The "separating system" can therefore also comprise a system consisting of multiple filters. Furthermore, the separating system comprises appropriate inlet and outlet connections for the sample and the reagents.

"Filter" is understood in this context to mean an element which makes it possible for the sample constituents with the nucleic acids to be amplified to be separated from other constituents of the biological sample. As a result of separation on the filter, said sample constituents are thus concentrated or accumulated. The sample constituents can be separated off both on the filter and within the filter material.

"Amplification" is understood to mean the specific increase in nucleic acid. This can, for example, occur by means of NASBA, RCA, LCR and/or PCR. "Direct amplification" is understood to mean the direct multiplication of the nucleic acid on or in the at least one filter, without the need beforehand for separate extraction of the nucleic acid, for example by cell lysis.

"Amplification reagents" are understood to mean all reagents required for carrying out the amplification, for example enzymes, buffers, nucleotides, primers and other auxiliary materials.

The term "extraction" or "to extract" is understood hereinafter to mean the process with which the nucleic acid to be amplified is made available for amplification.

Surprisingly, the method according to the disclosure makes it possible for sample constituents and the nucleic acids present therein to be concentrated and multiplied in only a few method steps. This is due, in particular, to the fact that the amplification takes place directly on the filter and a separate nucleic acid extraction step is not required, since the direct amplification comprises possible disruption of the sample constituents. Thus, a plurality of work steps can be omitted.

Furthermore, the work steps of accumulation, nucleic acid extraction, nucleic acid purification and amplification which are otherwise usually spatially separated can be carried out in one microfluidic system in which some steps even become redundant. As a result, the number of work steps and of the media used is markedly reduced, saving considerable time and cost.

Preferably, the sample constituents are cells or large virions such as the variola virion.

In one of the embodiments, the amplification in step 5) is carried out by PCR and comprises at least the following substeps:
5.1) modifying the filter, extracting nucleic acids and denaturing the at least one nucleic acid;
5.2) annealing primers; and
5.3) extending primers.

PCR has the advantage that the first PCR step, denaturation at about 95° C., reliably extracts the nucleic acids, i.e. makes them available for the amplification. This is particularly the case if the sample constituents are cells.

Modifying the filter ensures that, in the subsequent steps, neither the at least one nucleic acid nor PCR reagents are retained on the filter or bind to said filter and, as a result, impair and inactivate the amplification. Thus, modifying the filter leads to an improved PCR result. A separate extraction step, which is associated with laborious purification and rinsing procedures since it is necessary to inactivate the extraction reagents afterwards, is thus no longer required.

In a preferred embodiment, the filter is modified in step 5.1) by the addition of filter-blocking polymers in step 4), selected from the group consisting of soluble proteins or albumins, preferably BSA, or synthetic polymers, preferably PEG or PPG. The use of BSA shows, with respect to PCR, particularly good results.

In a further embodiment, the filter in step 3) is perfused laterally, i.e. the direction of flow of the sample is across or horizontal to the filter.

Lateral perfusion has the advantage that the structure of the separating system is far less complex than in the case of transversely constructed filter systems. Moreover, the perfusion distance through the filter is considerably lower. For example, by changing the direction of perfusion from transverse to lateral, it was possible to replace a 2-layer filter (Qiamp® Mini spin column) having a diameter of about 8 mm with a one-layer filter having an area of 3×16 mm or diameter of 8 mm, while maintaining the same level of separation. As a result, it was possible to reduce the filter volume considerably compared to transversely integrated filters, without having to accept losses in the level of separation. In microfluidic applications, this volume reduction is of considerable advantage, since the entire structure can be miniaturized. Furthermore, laterally perfused filters contribute to a simple, automatable procedure, considerably favoring a high yield of sample constituents and the subsequent amplification of the nucleic acid.

Whereas the term "separation rate" describes the number of sample constituents which are retained by the filter per unit of time, the "level of separation" or "efficiency" specifies the percentage of the sample constituents retained overall on the filter. In the case of a starting solution with 1000 sample constituents, 700 sample constituents retained by the filter correspond to a level of separation or efficiency of the filter of 70%.

In a further embodiment, a fiber filter is used as the laterally perfused filter. Although fiber filters have comparatively large pores, comparatively large amounts of sample constituents are separated off. In the case of membrane filters having pores of about 1 μm, only small amounts (<10%) of sample constituents having a diameter of about 1 μm can be separated off, whereas in the case of pore widths of <0.5 μm, significant separation rates can be achieved. In the case of laterally perfused fiber filters having fiber diameters of 1-10 μm and a porosity of 50-90%, it is possible, by contrast, to achieve a very high level of separation of well over 90%.

Alternatively, the fiber filter is perfused transversely.

In a further embodiment, the filter is selected from the group consisting of fiber filters, preferably silica-containing fiber filters, particularly preferably glass fiber filters, membrane filters and ion exchangers, preferably anion exchangers.

Preferably, use is made of silica-containing fiber filters whose glass fibers have a diameter between ≥0.01 μm and ≤40 μm, preferably between ≥0.1 μm and ≤30 μm, particularly preferably between ≥0.1 μm and ≤5 μm.

The preferred diameter depends, inter alia, on the diameter of the sample constituents to be concentrated.

Furthermore, it is also possible for the filter to comprise bulk material, i.e. to be a stationary phase.

Alternatively, use can also be made of membrane filters. In the case of membrane filters, filtration is achieved predominantly by means of the sieve effect. Preferably, use is made of membrane filters of the following type: Supor® 200 from Pall having a pore diameter of 0.22 μm. The pore widths of the membrane filters depend on the sample constituents to be filtered in each case. In the case of *E. coli* bacteria, a pore width of ≤1 μm is appropriate.

In addition, use can also be made of ion exchangers, more particularly anion exchangers. In the case of ion exchangers, strong interactions form between charged surface molecules of the sample constituents and the exchanger groups of the ion exchanger. An example here is the following type of anion exchanger: StratoSperes™ Ion Exchange SPE PL-MIXED MP from Varian Inc.

Surprisingly, the sample constituents can likewise be effectively separated off on fiber filters having comparatively large pores. This is particularly the case when the sample constituents are bacteria.

Moreover, fiber filters have the advantage that they—unlike membrane filters—also exhibit low flow resistance at a comparatively high load. In contrast, rapid clogging of the filter often occurs in the case of membrane filters, especially at high particle concentrations—this is because each separated-off sample constituent clogs a pore. Therefore, at the same pressure, the separation rate on membrane filters is lower than on fiber filters.

However, it is of course also possible to use a membrane filter and/or an ion exchanger—as described above—for carrying out the method according to the disclosure, since these filter types also exhibit high efficiencies of almost 100% and therefore ensure efficient separation of the sample constituents from the biological sample.

In a further embodiment, more than one filter is used in the method according to the disclosure. Preferably, two different filters are used, making it possible to separate off various sample constituents of different sizes.

In a further embodiment, the biological sample is a pathogen-containing sample fluid such as, for example, urine, blood, plasma, serum, swabs, saliva, sputum and/or bronchoalveolar lavage (BAL).

In a further embodiment, enzymatic, chemical and/or mechanical disruption of the sample constituents is carried out between steps 3) and 4), wherein the cell membrane or the virion envelope and/or the viral capsid are dissolved or damaged and the nucleic acids are made available as a result.

Accordingly, the term "disruption" is understood hereinafter to mean the process with which the nucleic acid to be amplified is made available for amplification. The terms "extraction" and "disruption" are thus the same in content, but the term "disruption" has been chosen in order to emphasize that a separate process is involved here which, unlike extraction, is not due to the amplification itself.

Said disruption is, for example, achieved by way of lysis, in which the nucleic acid is made available using enzymatic, thermal or chemical methods. Examples of enzymatic lysis methods are treatment with proteinase K or treatment with lysozyme. Thermal lysis is achieved by heating or freezing the sample constituents. Examples of chemical lysis methods are treatment with a combination of sodium dodecyl sulfate (SDS) and NaOH, treatment with guanidine thiocyanate (GIT) and treatment with a combination of Triton X100 and a high concentration of lithium chloride. Mechanical disruption is, for example, carried out using glass beads or a vortexer. In addition, there are yet further known disruption methods. A combination of the methods is likewise possible.

Additional disruption has the advantage that nucleic acid from sample constituents, in particular cells, which are difficult to disrupt is also made available for the subsequent amplification.

Preferably, the disruption step is enzymatic or chemical, since in this way no further instruments are required and the additional method step can be readily automated.

In a preferred embodiment, the at least one nucleic acid released as a result of the disruption of the sample constituents is purified prior to the amplification in step 5). This may be necessary depending on the amplification conditions, for example owing to a limited selection of primers in PCR amplification, in order to achieve an optimal amplification result. Purification can, for example, be carried out by rinsing with buffer solutions which, at the same time, set the optimal conditions for the subsequent amplification.

In a preferred embodiment, it is further envisaged that the nucleic acid amplified in step 5) is subsequently eluted from the filter. The term "to elute" refers to the detachment or removal of the nucleic acid from the filter. For this purpose, the filter is loaded with a mobile phase consisting of one or more solvents, and the nucleic acids are washed out with the eluate. This step should, for example, be carried out when the intended end application is the detection of the amplified nucleic acid on an array. Particular preference is given here to aqueous elution, i.e. elution of the amplified nucleic acid in deionized water.

Thus, if the amplification is carried out by means of PCR, the filter is preferably rinsed with a PCR buffer containing BSA after the capture of the sample constituents in order, for example, to remove impurities such as metabolites, to adjust the medium for subsequent PCR and to block the filter. Afterwards, a mixture of dNTPs, primers, polymerase and buffer is added, and the thermal cycles customary for PCR are carried out. In these temperature cycles, the DNA is amplified (multiplied). Subsequently, it can be eluted from the filter. For example, from 10 ml of urine containing $10^5$ pathogens, it is possible to isolate $10^{11}$ DNA molecules in 50 µl after 20 cycles.

Preference is also given to an embodiment in which the nucleic acid amplified in step 5) is rinsed off the filter with a precipitation solution and the eluate is mixed in a microfluidic system and applied again to the filter. The precipitation solution perfuses the filter preferably against the earlier direction of perfusion of the sample, and the mixed eluate perfuses the filter in the earlier direction of perfusion. This method step achieves purification of the amplified nucleic acid in order, for example, to improve a subsequent detection result. Suitable precipitation solutions are guanidine isothiocyanate (GIT) and/or ethanol. Mixing in a microfluidic system can be carried out by means of magnetic beads and/or mixer structures with, for example, wash buffers.

Alternatively, chromatographic purification of the nucleic acids is also conceivable.

A further alternative possibility is to apply the eluate to a fresh filter after precipitation. This step is useful for certain applications, for example when there are special requirements with regard to DNA purity.

As already mentioned, the filter can comprise bulk material or a stationary phase. In such a case, it is preferably envisaged that the nucleic acid amplified in step 5) is rinsed off the filter with a precipitation solution and the eluate is mixed in a microfluidic system and applied again to the filter. The precipitation solution perfuses the stationary phase against the earlier direction of perfusion, and the mixed eluate perfuses the stationary phase in the earlier direction of perfusion. Suitable selection of the stationary phase thus makes chromatographic purification possible.

The present disclosure further relates to an apparatus for carrying out the method according to the disclosure, which apparatus is in the form of a lab-on-a-chip system.

The apparatus makes it possible to carry out the method according to the disclosure in a µ-TAS system, starting from macroscopic sample volumes. Thus, despite large sample volumes with a high concentration of sample constituents to be accumulated, miniaturization becomes possible, which in turn can be used in a manner saving time and cost.

BRIEF DESCRIPTION OF THE DRAWINGS

Further advantages and advantageous embodiments of the method according to the disclosure are illustrated by the figures and exemplary embodiments and explained in the following description. It should be noted that the figures and exemplary embodiments are only descriptive in character and are not intended to limit the disclosure in any way. The figures use the following reference symbols.

DETAILED DESCRIPTION

Figure 1:
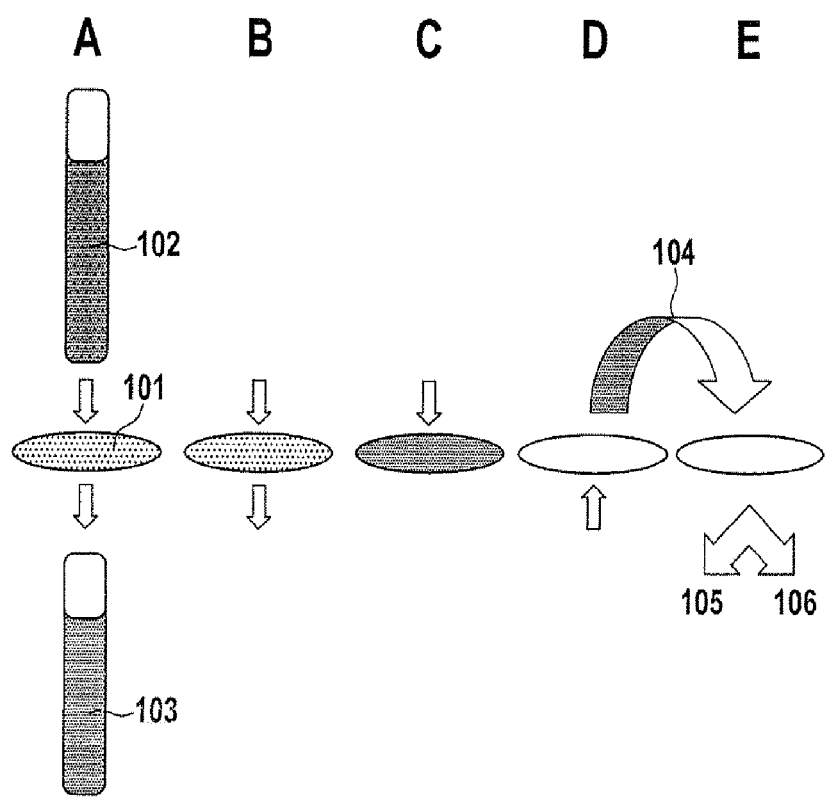
FIG. 1 shows a flow diagram of the method according to the disclosure.

FIG. 1 shows a flow diagram of the method according to disclosure using a separating system.

The biological sample, for example urine, with the pathogens present therein, for example $E.$ $coli$ bacteria, is applied to a filter. The nucleic acid to be amplified is DNA, and the amplification is carried out by means of PCR.

In step A, a macroscopic sample volume (10 ml) of a bacterial suspension 102 containing $10^4$ to $10^7$ bacteria/ml is conducted over a filter, in this case a silica fiber pad, 101 for 10 min (i.e. 1 ml/min) at a pressure of up to 0.5 bar. The $E.$ $coli$ bacteria are retained on the silica fiber pad, with the level of separation being 95%-99%, and so the suspension 103 subsequently contains virtually no bacteria 102. After that, the filter 101 is washed with 100-500 µl of PCR buffer in step B in order to obtain optimal conditions for PCR. In step C, the PCR solution—in this case 30 µl of PCR master mix with dNTPs, buffer, Taq polymerase, primers and PEG—is added, and the PCR cycles are started. During the PCR reaction, the first denaturation step results in lysis of the $E.$ $coli$ bacteria 102. Step D shows the first part of the purification—the precipitation—of the amplified DNA, which is carried out against the earlier direction of perfusion. The eluate is mixed in a microfluidic system using a mixer indicated by the arrow 104 and applied again to the filter. In the final step E, the precipitated DNA is applied again to the filter 101 in the direction of perfusion. After rinsing with wash buffers, which are drained into a waste container indicated in the figure by no. 105, the purified DNA is eluted in 50 µl of hybridization buffer (indicated by arrow 106). The DNA can then be used directly for hybridization.

Figure 2:
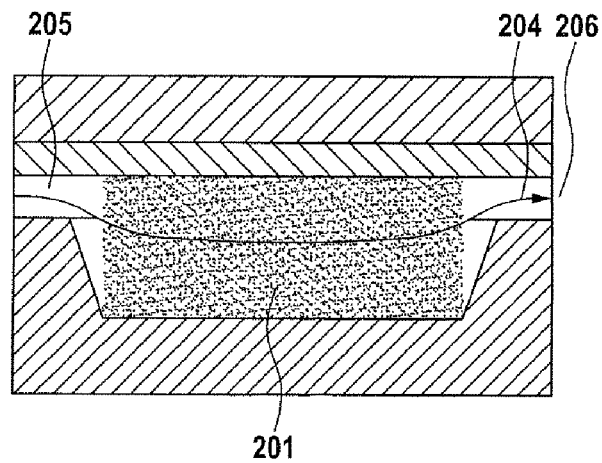
FIG. 2 shows a separating system having a laterally perfused fiber filter 201.

FIG. 2 shows a separating system having a laterally perfused fiber filter 201. Arrow 204 indicates the direction of perfusion of the sample during separation on the filter as per step 3) of the method according to the disclosure. The separating system has an inlet 205 and an outlet 206 for the sample and reagents.

In the separating system having a laterally perfused fiber filter 201, the biological sample, for example a saliva sample containing virally attacked cells, is injected into the separating system at the inlet 205 and then conducted over or through the filter 201 in the direction of perfusion 204, with the cells being retained by the filter 201. The rest of the saliva sample leaves the separating system via the outlet 206. As a result, the virally attacked cells are accumulated or concentrated. In the next step (not shown), amplification reagents, including special primers and a substance which blocks the filter 201, are added. Subsequently, the released viral nucleic acid is amplified on or in the filter 201 using the special primers, which are specific for the viral nucleic acid, with the nucleic acid extraction, in this case cell lysis, taking place in the first amplification step.

Figure 3:
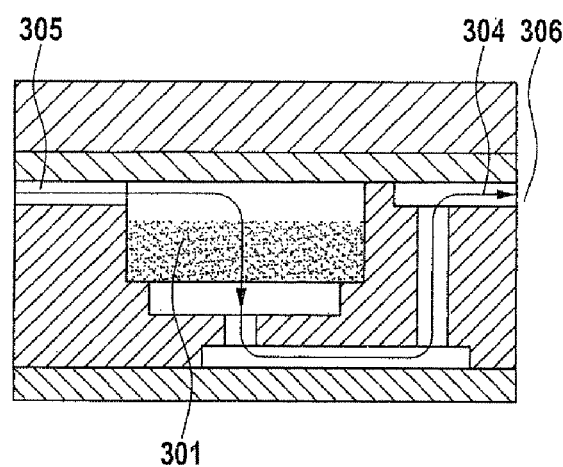
FIG. 3 shows a separating system having a transversely perfused filter 301.

FIG. 3 shows a separating system having a transversely perfused filter 301.

Arrow 304 indicates the direction of perfusion of the sample during separation on the filter as per step 3) of the method according to the disclosure. The separating system has an inlet 305 and an outlet 306 for the sample and reagents. In the separating system having a transversely perfused filter 301, the cells, for example $Staphylococcus$ $aureus$ bacteria from a BAL sample, are introduced into the separating system via the inlet 305. The bacteria are conducted transversely through or onto the filter 301 in the direction of perfusion 304, with the bacteria being retained by the filter 301. The rest of the BAL sample leaves the separating system via the outlet 306. As a result, the bacteria are accumulated or concentrated. In the next step (not shown), the bacteria are lysed. After addition of the amplification reagents, the bacterial nucleic acid is amplified in the filter 301.

Test 1:

The test clarified whether a separate extraction or lysis step can be omitted and PCR can be carried out on the filter and whether successful hybridization is ultimately possible.

For the PCR on the filter, use is made of a reverse primer which is labeled at the 5' end with the fluorescent molecule Cyanine 3.

The test is carried out with $10^7$ $E.$ $coli$ cells, which are centrifuged (6000 rpm, 15 sec) onto one half of a crushed filter from the Qiagen QIAamp® Mini Spin Kit. Afterwards, the filter pieces are transferred to a PCR vessel and the PCR mix (with BSA) is added.

TABLE 1

| | PCR mix | | |
|---|---|---|---|
| Reagent | 1x Mix | 3x Mix | Final concentration |
| Forward primer (2 µM) | 2.5 µl | 7.5 µl | 0.2 µM |
| Reverse primer (2 µM) | 2.5 µl | 7.5 µl | 0.2 µM |
| dNTP mix (2.5 mM) | 1 µl | 3 µl | 0.1 mM |
| Taq polymerase (5 U/µl) | 0.5 µl | 1.5 µl | 0.1 U/µl |
| Taq buffer (10x) | 2.5 µl | 7.5 µl | 1x |
| MgCl$_2$ (25 mM) | 1.5 µl | 4.5 µl | 1.5 mM |
| BSA (20 mg/ml) | 6.25 µl | 18.75 µl | 5 mg/ml |
| HPLC H$_2$O | 8.25 µl | 24.75 µl | |
| Total volume | 25 µl | 75 µl | |

TABLE 2

PCR program

| Step | Temperature | Duration |
| --- | --- | --- |
| 1 - Initial denaturation | 95° C. | 5 min |
| 2 - Denaturation | 95° C. | 30 sec |
| 3 - Primer annealing | 55° C. | 1 min |
| 4 - Primer extension | 72° C. | 1 min |
| 30 cycles: steps 2 to 4 | | |
| 5 - Terminal extension | 72° C. | 10 min |

The PCR solution is removed from the filter by centrifugation for 15 s at 6000 rpm. The hybridization mix is then added to the solution obtained.

TABLE 3

Hybridization mix

| Reagent | 1x Mix | 3x Mix | Final concentration |
| --- | --- | --- | --- |
| H$_2$O | 16 µl | 48 µl | |
| 20x SSPE | 21 µl | 63 µl | 6x |
| 50x Denhardt's solution | 7 µl | 21 µl | 5x |
| Hyb. con. (0.001 pmol/µl) | 1 µl | 3 µl | 0.001 pmol |
| PCR product | (25 µl) | (75 µl) | |
| Total volume | 70 µl | 210 µl | |

Hybridization Control (Hyb. Con.):

The hybridization control consists of a sequence from *Arabidopsis thaliana* and is complementary to the immobilized positive hybridization control. This control DNA is modified with biotin. The positive hybridization control always produces a signal under good hybridization conditions.

Carrying Out the Hybridization
  Each PCR solution (about 25 µl) is admixed with 45 µl of the hybridization master mix
  The samples are heated at 95° C. for 10 min, and then immediately placed on ice
  Sticking on the Gene Frames
  Pipetting the hybridization mix
  Sealing with a cover slip and watching out for air bubbles
  Hybridization at 55° C. and 1400 rpm on a Thermomixer for one hour After the hybridization, the slides are washed and the Gene Frames and slides are detached in about 300 ml of wash solution 1 (2×SSC, 0.2% SDS). This is then followed by three incubation steps before the slides are dried by blowing with nitrogen and analyzed.

Figure 4:
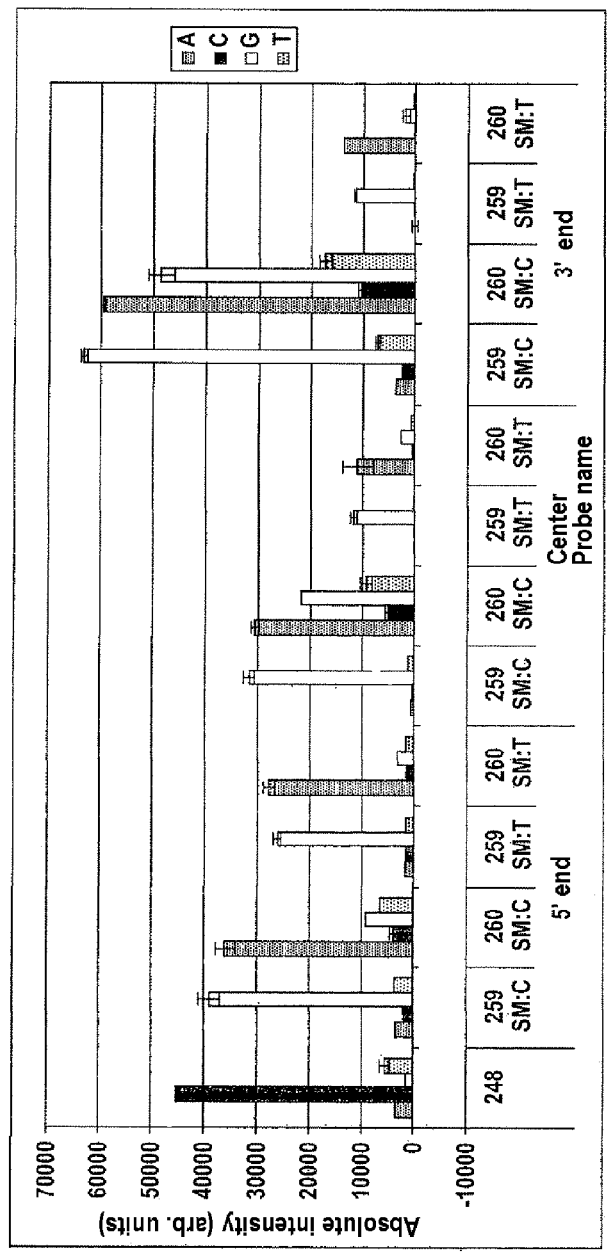
FIG. 4 shows the test result for sample 1 in the exemplary embodiment—labeled primers, filter PCR, $10^7$ cells, 25 µl.

Results:

FIG. 4 shows the test result for sample 1—labeled primers, filter PCR, 10$^7$ cells, 25 µl.

The X-axis displays tests with different probes. The first field displays the intensities of a hybridized probe consisting of the nucleotides complementary to bases 237-252, with position 248 (wild type: C; fluoroquinolone-resistant: T or G) varying by all 4 bases. Only the perfect match C in the wild type shows a high intensity. In the next block, probes reflecting bases 254 to 273 were varied by all 4 bases close to the 5' end in positions 259 and 260, with two silent mutations in position 255 also being shown (SM:C and SM:T). In the wild type, bases G and A are present in positions 259 and 260. By contrast, in the quinolone-resistant strains, A, T or C, and G or T, respectively, are present. It was found for the wild type that there are good selectivities for the perfect match over the mismatch, independent of the silent mutation in position 255.

By contrast, if bases 259 and 260 are instead arranged more in the center of the probe or at the 3' end of the probe, considerably poorer selectivities are observed. Here, it is no longer possible to reliably differentiate mutations at position 260 with SM$_{255}$:C.

Figure 5:
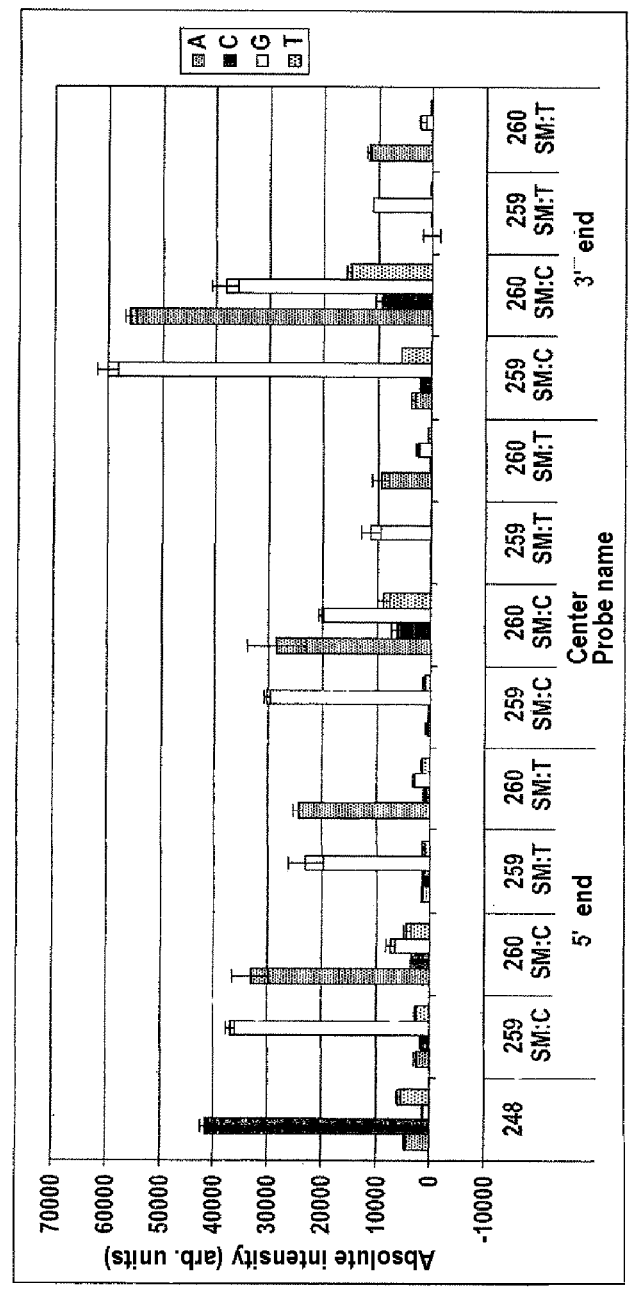
FIG. 5 shows the test result for sample 2 in the exemplary embodiment—labeled primers, filter PCR, $10^7$ cells, 25 µl.

FIG. 5 shows the test result for sample 2—labeled primers, filter PCR, 10$^7$ cells, 25 µl As for FIG. 4, there is displayed, with bases 248:C, 259:G and 260:A, the analysis of a quinolone-resistant bacterium. Here as well, the selectivity following arrangement of bases 259 and 260 at the 5' end of the probe is suitable for reliable detection, whereas probes having these mutations in the center of the probe or at the 3' end are not suitable.

Figure 6:
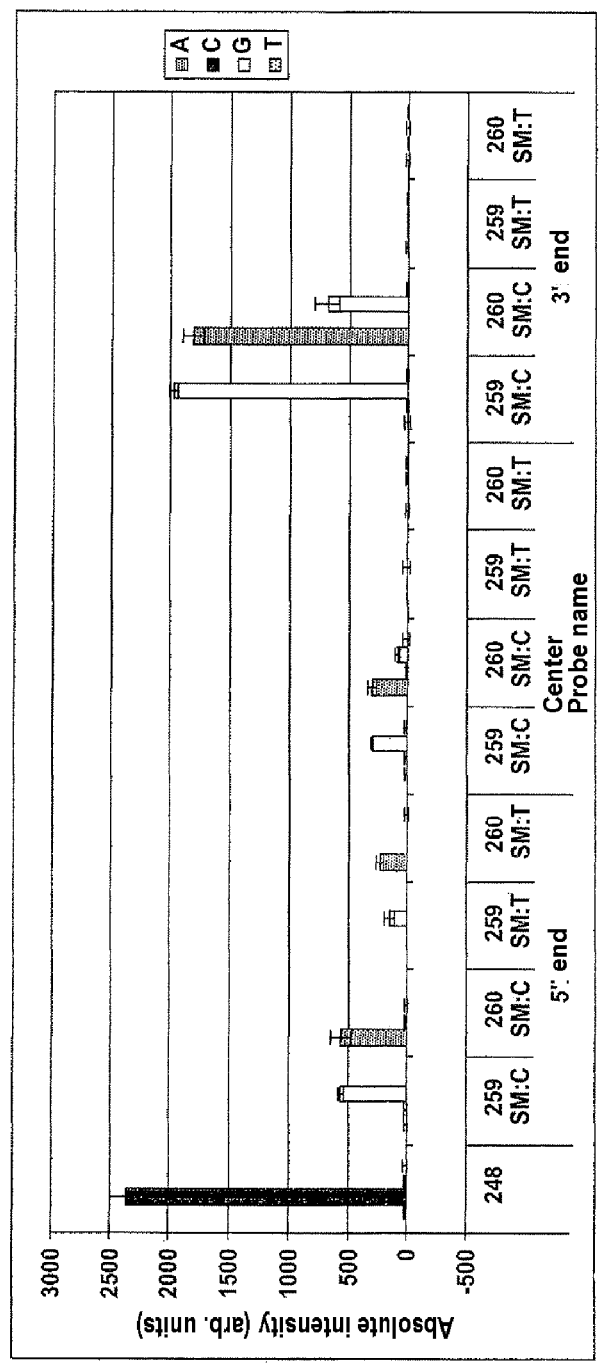
FIG. 6 shows the test result for the test for establishing the detection limit.

FIG. 6 shows the test result for the test for establishing the detection limit.

As for FIG. 5, there is displayed an analysis of a test series, having a very low bacterial concentration. The bacterial concentration here is in a range between 10$^3$ and 10$^4$/ml and therefore represents the diagnostically relevant lower detection limit.

Figure 7:
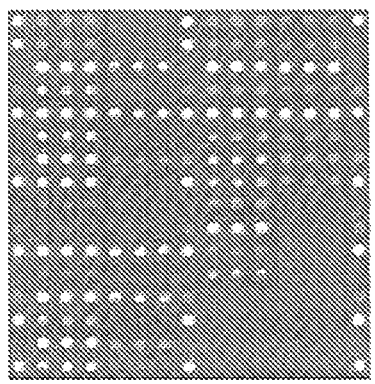
FIG. 7 shows the hybridization patterns for samples 1 to 3 from FIGS. 1 to 3 in the exemplary embodiment.
Figure 7:
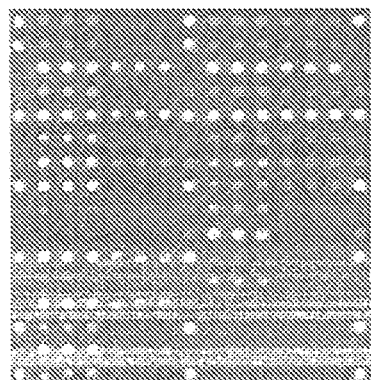
Figure 7:
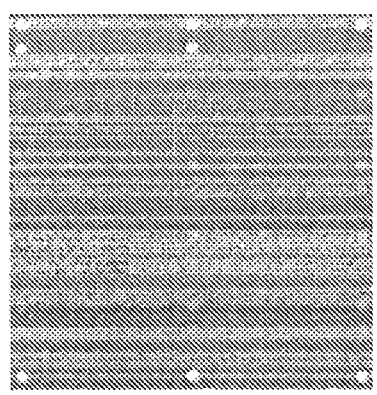

FIG. 7 shows the hybridization patterns for samples 1 to 3 from FIGS. 4 to 6, where FIG. 7A corresponds to the hybridization pattern for sample 1, FIG. 7B corresponds to the hybridization pattern for sample 2, and FIG. 7C corresponds to the hybridization pattern for the test for establishing the detection limit.

The results show in principle that a separate extraction or lysis step can be omitted and PCR can be carried out on the filter and that successful hybridization is ultimately possible.

Test 2:

In the test, *E. coli* bacteria having a diameter of about 1 µm are separated off on a fiber filter having fiber diameters of 0.1-10 µm and a porosity of 90-96%. The level of separation is well over 90%.

It is thus apparent that fiber filters, in particular those consisting of silica fibers or glass fibers, have an extremely high level of separation of, in general, well over 95% at very high flow rates and low flow resistances. The filtration mechanism can be attributed to polar interactions of the bacteria with the filter surface and to the sieve effect.

What is claimed is:

1. A method for concentrating sample constituents and for multiplying nucleic acids from a biological sample which are contained in the sample constituents, comprising:
  1) providing a biological sample in liquid form;
  2) introducing the sample into a separating system having at least one filter;
  3) accumulating the sample constituents contained in the sample by separating off the sample constituents on the filter;
  4) adding amplification reagents to the separating system; and
  5) directly amplifying at least one nucleic acid present in the sample constituents;
  wherein the amplification in step 5) is carried out by PCR and comprises at least:
    5.1) extracting nucleic acids without using chemical lysing agents and denaturing the at least one nucleic acid;
    5.2) annealing primers; and
    5.3) extending primers.

2. The method according to claim 1, wherein the filter is modified in step 5.1) by the addition of filter-blocking polymers in step 4), selected from the group consisting of soluble proteins, albumins, and synthetic polymers.

3. The method according to claim 1, wherein the filter in step 3) is perfused laterally.

4. The method according to claim 1, wherein the filter is selected from the group consisting of
fiber filters,
membrane filters, and
ion exchangers.

5. The method according to claim 1, wherein the nucleic acid amplified in step 5) is subsequently eluted from the filter.

6. The method according to claim 1, wherein the nucleic acid amplified in step 5) is rinsed off the filter with a precipitation solution and the eluate is mixed in a microfluidic system and applied again to the filter.

7. The method according to claim 6, wherein the precipitation solution perfuses the filter against the earlier direction of perfusion and the mixed eluate perfuses the filter in the earlier direction of perfusion.

8. The method according to claim 2, wherein the albumin is BSA.

9. The method according to claim 2, wherein the synthetic polymer is PEG or PPG.

10. The method according to claim 4, wherein the fiber filter is a silica-containing fiber filter or a glass fiber filter.

11. The method according to claim 4, wherein the ion exchanger is an anion exchanger.

12. The method according to claim 1, wherein the step of extracting nucleic acids is accomplished by the denaturation step of the PCR.

13. The method according to claim 12, wherein the denaturation step of the PCR takes place at about 95° C.

* * * * *